US007238172B2

(12) United States Patent
Bertheas

(10) Patent No.: US 7,238,172 B2
(45) Date of Patent: Jul. 3, 2007

(54) DEFORMABLE MEDICAL DEVICE FOR REMOVING A NEEDLE

(75) Inventor: Jacques Bertheas, Lissieu (FR)

(73) Assignee: Districlass Medical SA, Corbas (FR)

( * ) Notice: Subject to any disclaimer, the term of this patent is extended or adjusted under 35 U.S.C. 154(b) by 284 days.

(21) Appl. No.: 10/514,193

(22) PCT Filed: May 16, 2003

(86) PCT No.: PCT/FR03/01490

§ 371 (c)(1),
(2), (4) Date: Nov. 12, 2004

(87) PCT Pub. No.: WO03/097119

PCT Pub. Date: Nov. 27, 2003

(65) Prior Publication Data

US 2005/0177113 A1 Aug. 11, 2005

(30) Foreign Application Priority Data

May 17, 2002 (FR) .................................. 02 06091

(51) Int. Cl.
*A61M 5/32* (2006.01)
*A61M 31/00* (2006.01)
*A61M 37/00* (2006.01)

(52) U.S. Cl. ................ 604/174; 604/177; 604/288.01; 604/288.04

(58) Field of Classification Search ................ 604/117, 604/288.01–288.04, 174–180, 96.01, 164.01, 604/164.04, 164.08, 164.12, 264
See application file for complete search history.

(56) References Cited

U.S. PATENT DOCUMENTS 3,459,175 A * 8/1969 Miller ........................ 600/431
4,579,120 A * 4/1986 MacGregor ................. 600/392
4,632,671 A * 12/1986 Dalton ....................... 604/174
4,861,341 A * 8/1989 Woodburn .................. 604/175
4,986,819 A 1/1991 Sobel
5,073,169 A * 12/1991 Raiken ....................... 604/180
5,078,685 A * 1/1992 Colliver ................. 604/103.07
5,224,936 A * 7/1993 Gallagher .................. 604/192
5,400,773 A * 3/1995 Zhu et al. ................... 600/207
5,620,419 A * 4/1997 Lui et al. .................... 604/116

FOREIGN PATENT DOCUMENTS

EP 0 821 974 2/1998
WO WO 98 34675 8/1998

* cited by examiner

*Primary Examiner*—Kevin C. Sirmons
*Assistant Examiner*—Elizabeth MacNeill
(74) *Attorney, Agent, or Firm*—Young & Thompson

(57) ABSTRACT

The invention concerns a medical device comprising an inflatable sheath (2), a tubing (3) integral with a non-return valve (4), a rigid disc (5) forming a horizontal platform above the chamber (2) and means for receiving (6, 7, 18) the cannula (13, 20).

13 Claims, 5 Drawing Sheets

FIGURE 4
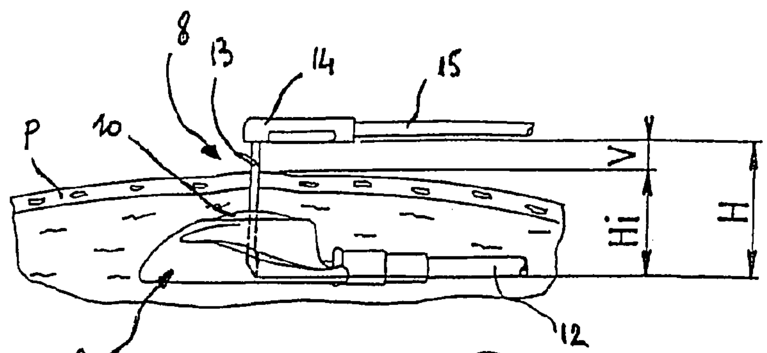
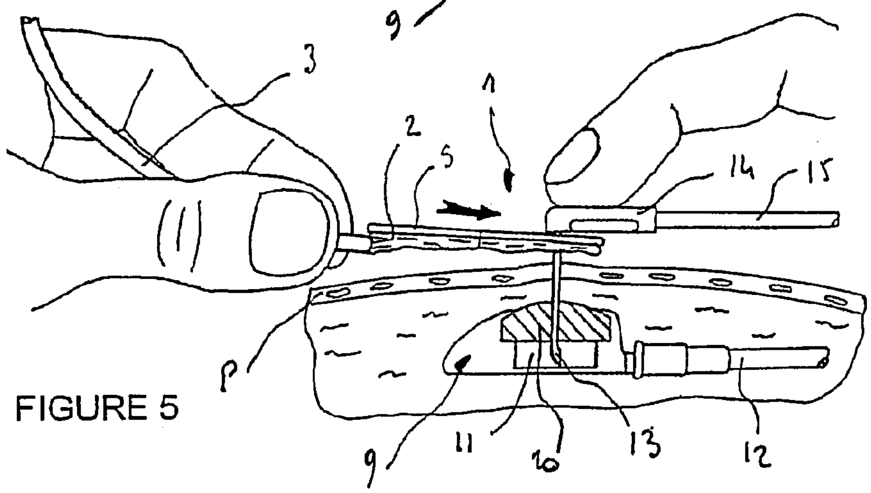
FIGURE 5
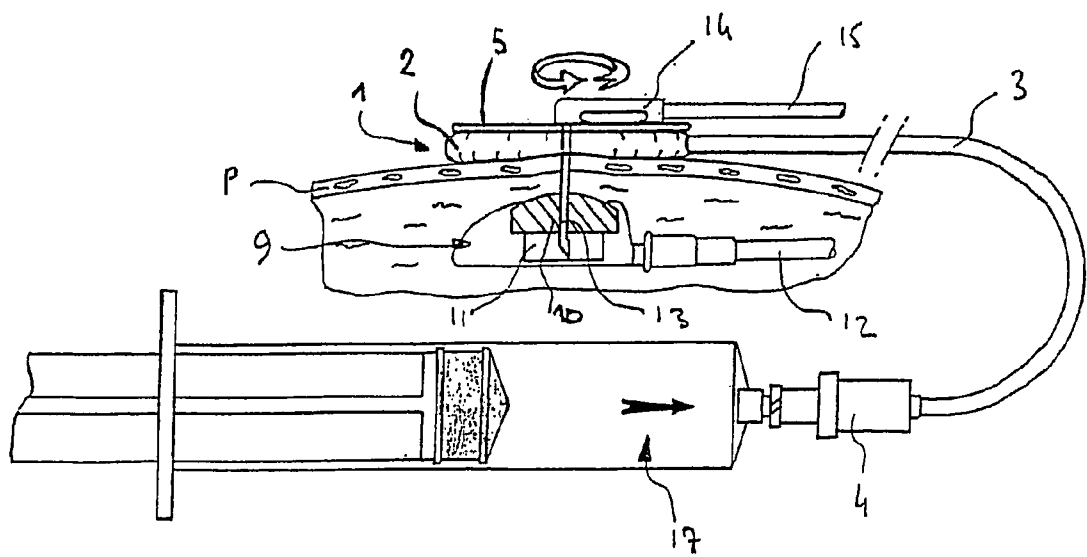
FIGURE 6

1
2
5
19
21
20
P
9
3
10
11
12
4
22
23

1
2
5
20
19
21
P
9
3
10
11
12
4
22
23

5
19
21
2
20
1
3
9
12
10
11
4
22
23

DEFORMABLE MEDICAL DEVICE FOR REMOVING A NEEDLE

The present invention relates to a medical device which is elastically deformable under the action of pressurized air or liquid, so as to permit removal of a needle and, more particularly, of a Huber needle.

It has been noted that, in order to remove an implanted needle, medical teams apply a tractive force which, immediately after extraction of the needle, causes a rebound effect which poses a risk of needlestick injury to the fingers of the members of the medical team situated in proximity to the needle.

Thus, the medical device according to the present invention makes it possible to form, around the needle, an inflatable sheath permitting protection of the personnel's fingers and gradual and unforced removal of said needle from an implantable chamber, for example.

Likewise, the medical device according to the present invention ensures patient comfort by providing a sheath under the needle throughout the period of the implantation.

The medical device according to the present invention comprises an inflatable sheath connected to a tubing, said sheath comprising at least one receiving space for the passage of the cannula.

The medical device according to the present invention comprises an inflatable sheath connected to a tubing, and a rigid disk forming a horizontal platform arranged and fixed above the sheath.

The medical device according to the present invention comprises an inflatable sheath and a rigid disk with, respectively, receiving spaces for the passage of the cannula.

The medical device according to the present invention comprises a sheath which, starting from its center and extending toward the outside, has a receiving space formed by a slit creating two separate and leaktight ends, so that said sheath has a C-shaped profile.

The medical device according to the present invention comprises a sheath having a receiving space of annular shape.

The medical device according to the present invention comprises a rigid disk which, starting from its center, has a slit with a V-shaped profile whose most open base is arranged toward the periphery of said disk.

The medical device according to the present invention comprises a rigid disk fixed in the upper part of the sheath in such a way that its center coincides with that of said sheath.

The medical device according to the present invention comprises a rigid disk integral with a body connected to a tapered cannula which traverses said disk so as to cooperate inside a free space formed in the sheath.

The medical device according to the present invention comprises a connection piece which, perpendicular to the tapered cannula, has a tubing whose free end is integral with a non-return valve.

The following description given with reference to the attached drawings and by way of nonlimiting examples will permit a better understanding of the invention, its characteristics, and the advantages it is likely to afford.

FIGS. 4 through 9 are views showing the different stages in the use of the medical device from FIGS. 1 through 3.

Figure 1:
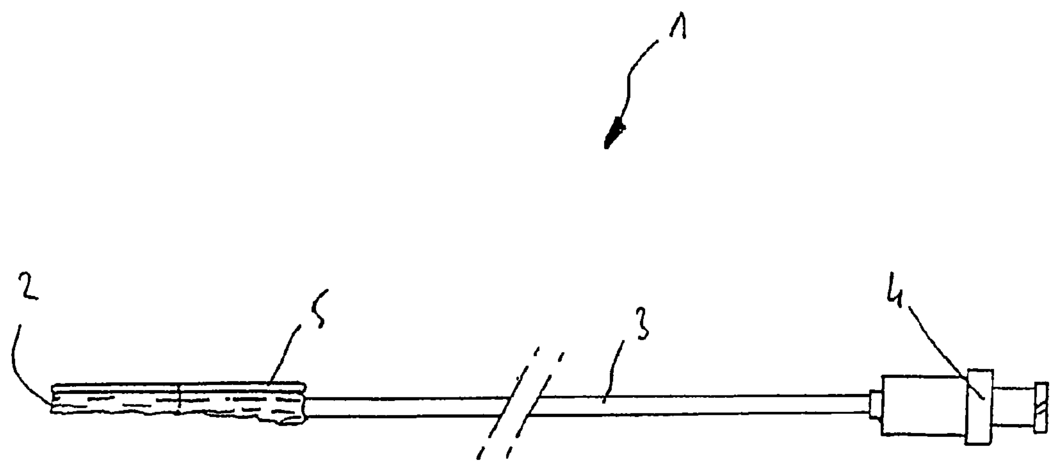
FIG. 1 is a side view showing the medical device according to the present invention in a rest position.
Figure 2:
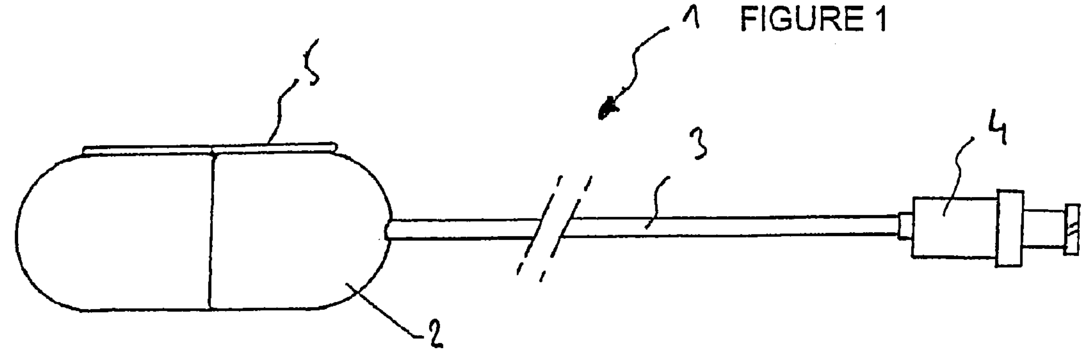
FIG. 2 is a side view illustrating the medical device according to the present invention when inflated.
Figure 3:
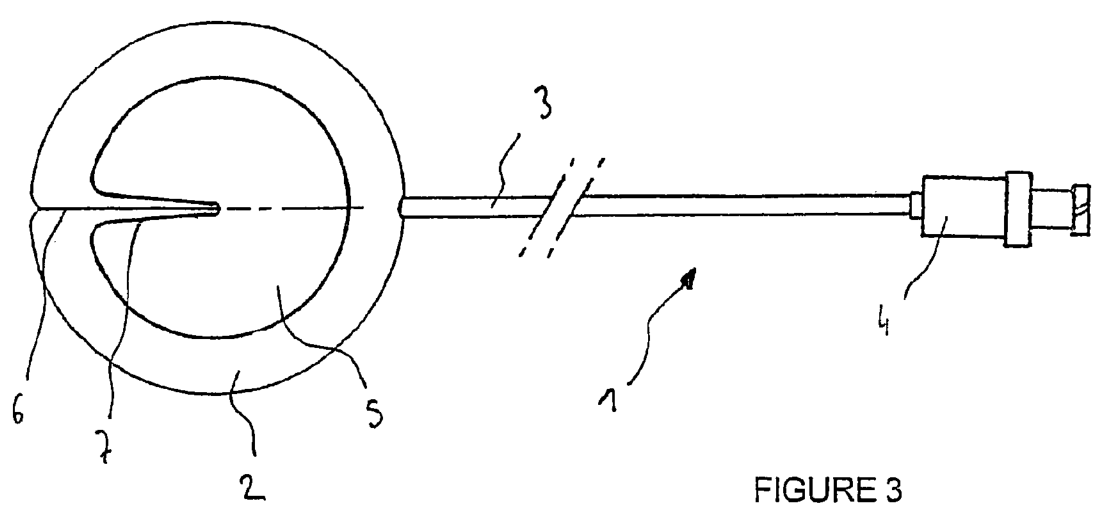
FIG. 3 is a plan view showing the medical device according to the invention when inflated.
Figure 7:
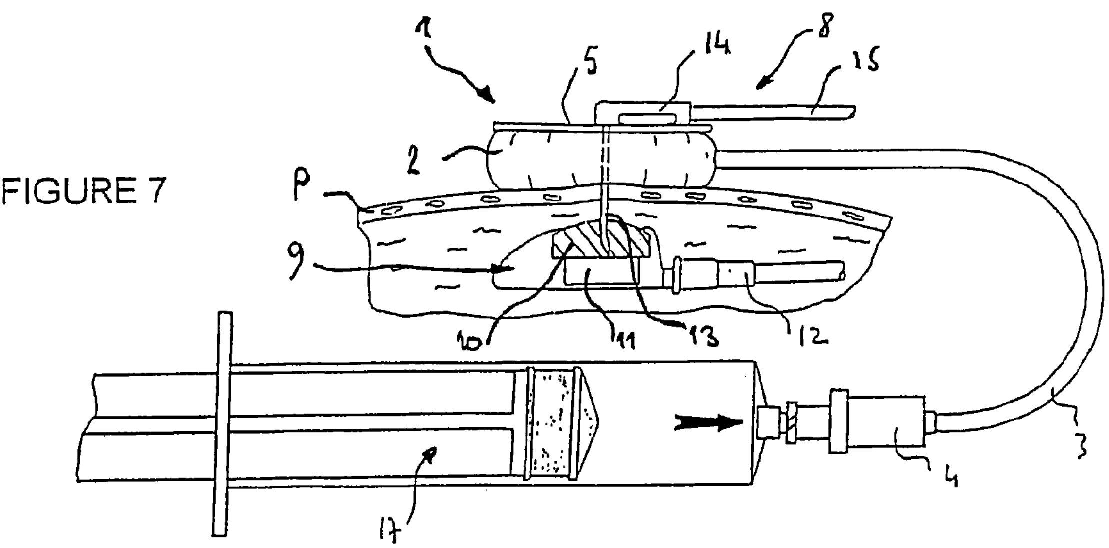
Figure 8:
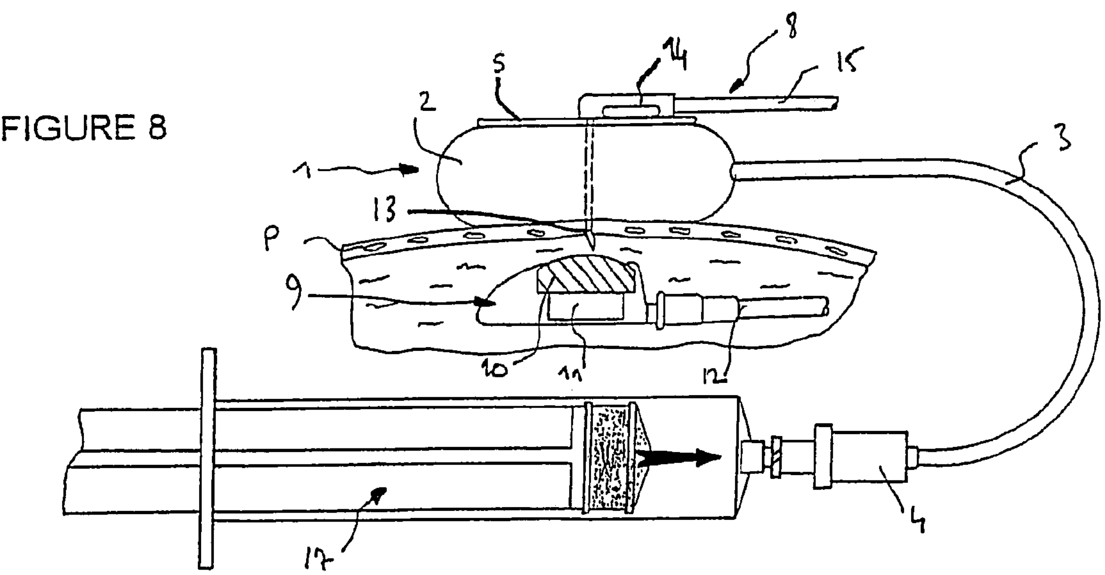
Figure 9:
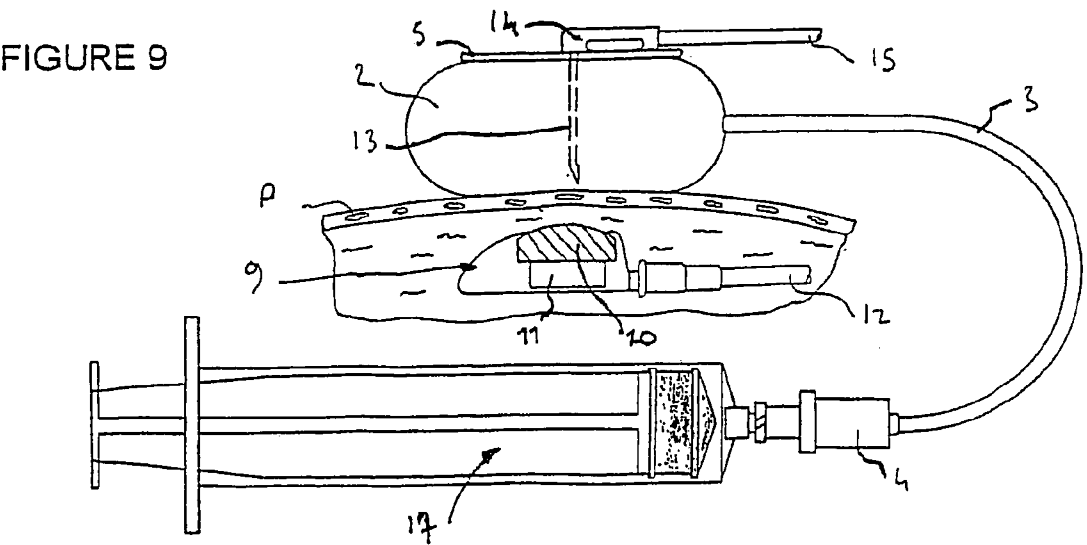

In FIGS. 1 through 3, a medical device 1 has been shown which comprises a leaktight sheath 2 which is deformable under the effect of an external pressure, and a tubing 3 integral with a non-return valve 4.

At the end remote from the non-return valve 4, the tubing 3 communicates in a leaktight manner with the inside of the sheath 2 so that it is possible to inflate the latter by means of pressurized air or liquid.

The medical device 1 can comprise, above the sheath 2, a rigid disk 5 forming a horizontal platform ensuring distribution of the pressure forces during inflation of said chamber.

Starting from its center and extending toward the outside, the sheath 2 comprises a slit 6 forming two separate and leaktight ends so that said sheath has a C-shaped profile.

The rigid disk 5 is fixed on the sheath 2 in such a way that its center coincides with that of said chamber.

Starting from its center, the rigid disk 5 comprises a slit 7 with a V-shaped profile whose most open base is arranged toward the periphery of said disk.

The slit 7 of the rigid disk 5 is provided above that 6 of the sheath 2 of the medical device 1.

It will be noted that the tubing 3 is carried, for example, on the same axis as that of the slits 6, 7 of the sheath 2 and of the rigid disk 5.

FIGS. 4 through 9 show the different stages in the use of the medical device 1 according to the present invention for removing a Huber needle 8 from an implantable chamber 9, for example.

The chamber 9 is implanted under a patient's skin P, for example for treatment in the form of chemotherapy.

The chamber 9 is connected to the outside by way of the Huber needle 8 which traverses a membrane 10 and opens out inside a recess 11.

The latter is connected by way of a catheter 12 to one of the patient's vessels in order to permit injection of treatment products.

Figure 10:
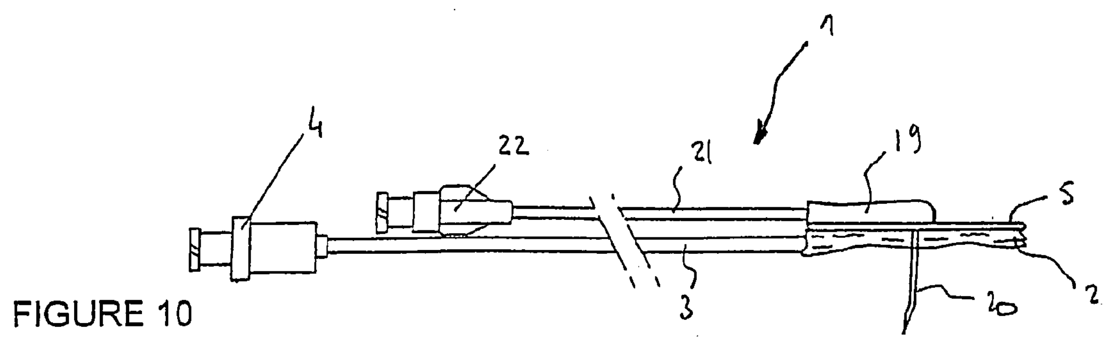
FIG. 10 is a side view showing a variant of the medical device according to the present invention in the rest position.

The Huber needle 8 comprises a tapered cannula 13 around which a body 14 of any desired shape is molded in the area remote from the tip and in a direction perpendicular to the axis of said cannula, said body 14 being connected in a leaktight manner to a tubing 15 integral with a connection system similar, for example, to the system 22 (FIG. 10).

When the Huber needle 8 is introduced inside the chamber 9, it will be noted that:

- the height between the lower face of the body 14 and the tapered tip of the cannula 13 is H,
- the depth of implantation of the needle beneath the skin P, to the bottom of the recess 11 of the chamber 9, is Hi,
- the height of the space between the outer face of the skin P and the lower face of the body 14 is V.

Method of Use

The medical device 1 and more particularly the sheath 2 integral with the rigid disk 5 is placed in the space V provided between the patient's skin P and the lower face of the body 14 of the Huber needle 8.

The medical device 1 is introduced via an access route which is located, for example, opposite the tubing 15 of the Huber needle 8, or via any other route not located in the axis of said tubing 15.

The medical device 1 is positioned in the space V in such a way that the cannula 13 of the Huber needle 8 cooperates with the slits 6 and 7 of the sheath 2 and of the disk 5.

The medical device 1 is correctly positioned when the cannula 13 is placed in the bottom of each slit 6, 7, that is to say when the cannula 13 is carried by the vertical and central axis of the sheath 2 and of the disk 5.

The medical device 1 is then driven in rotation around the cannula 13 of the Huber needle 8 in order to orient the tubing 3 of said device toward the tubing 15 of said needle, so as to improve patient comfort.

The medical device 1 and more particularly the sheath 2 is inflated by means of a liquid or air injected through a syringe 17 connected to the non-return valve 4 integral with the tubing 3.

The volume of the sheath 2 is inflated in order initially to fill the space V and then increased gradually in order to remove the cannula 13 of the Huber needle 8 from the membrane 10 of the implantable chamber 9 and from the patient's skin P.

Thus, by virtue of the vertical displacement of the disk 5 during the increase in volume of the sheath 2, the medical device 1 permits gradual removal of the Huber needle 8 without risk of any rebound phenomenon and, consequently, without risk of the medical personnel being pricked or injured.

It will also be noted that the sheath 2 of the medical device 1 forms a protective element around the cannula 13 of the Huber needle 8 and limits the risk of the medical staff suffering a needlestick injury.

Figure 11:
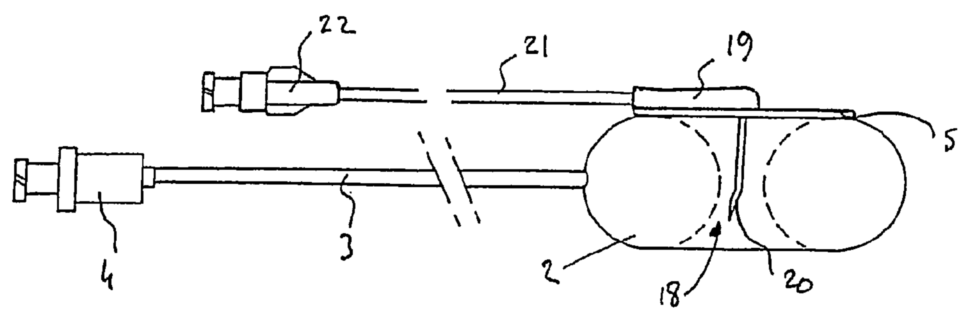
FIGS. 11 and 12 are views illustrating the medical device from FIG. 10 according to the present invention when inflated.
Figure 12:
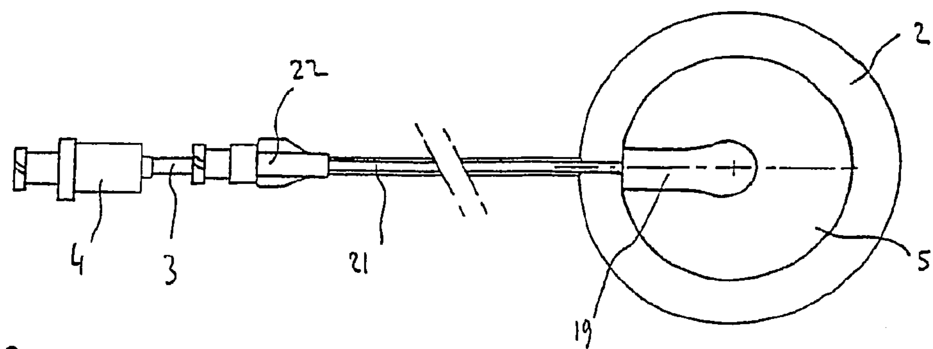

FIGS. 10 through 12 show a variant of the medical device 1 which comprises a sheath 2 deformable under the effect of an external pressure, a tubing 3 integral with a non-return valve 4, and a tapered cannula 20 forming a needle.

At the end remote from the non-return valve 4, the tubing 3 communicates in a leaktight manner with the inside of the sheath 2, in order to be able to inflate the latter by means of pressurized air or liquid.

Above the sheath 2, the medical device 1 comprises a rigid disk 5 forming a horizontal platform for distributing the pressure forces during inflation of said sheath 2.

In the inflated position, the sheath 2 has a defined volume of annular shape with, at its center, a free space 18 passing vertically through the medical device 1.

The rigid disk 5 is fixed in the upper part of the sheath 2 in such a way that its center coincides with that of said sheath 2. Facing away from the sheath 2, the disk 5 is integral with a body 19 connected to a tapered cannula 20 passing through said disk so as to cooperate inside the free space 18 of the sheath 2.

The body 19 comprises, perpendicular to the cannula 20, a tubing 21 whose free end is integral with a connection system 22. The tubing 21 is arranged above the tubing 3, and in a plane parallel to that containing the tubing 3, for supplying the sheath 2.

Figure 13:
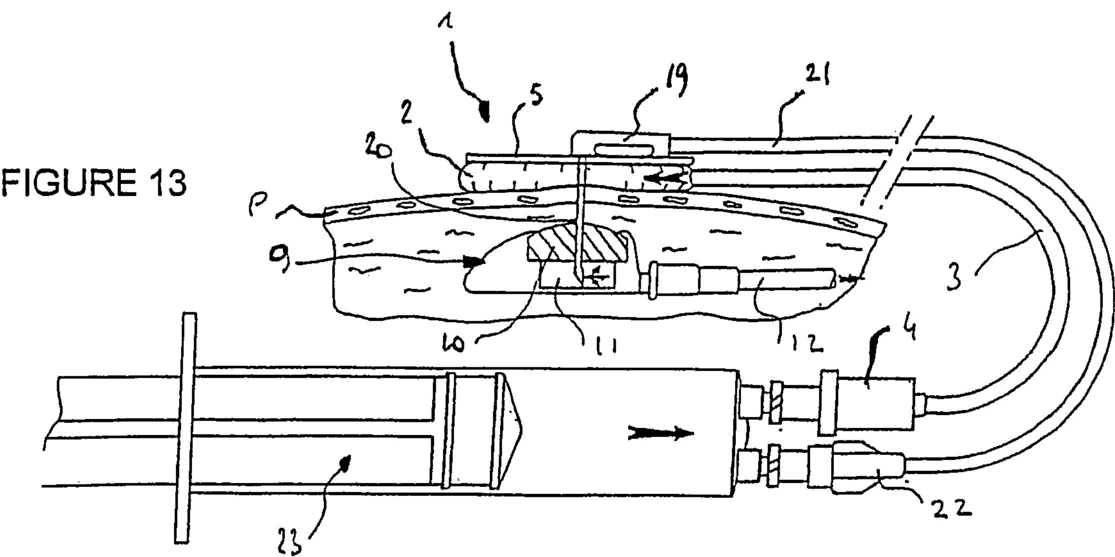
FIGS. 13 through 15 are views showing the different stages in the use of the variant of the medical device from FIGS. 10 through 12.
Figure 14:
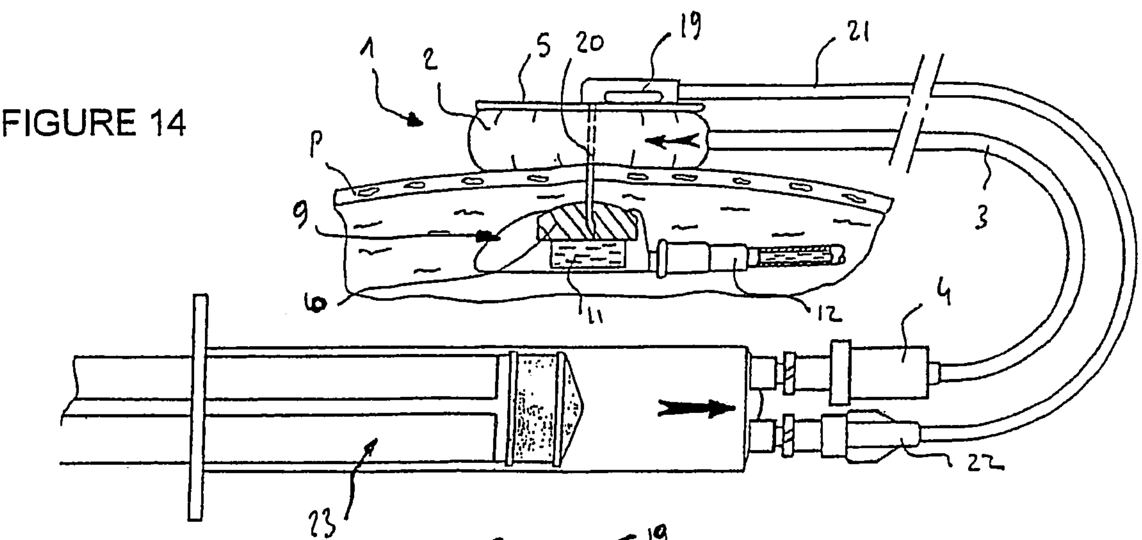
Figure 15:
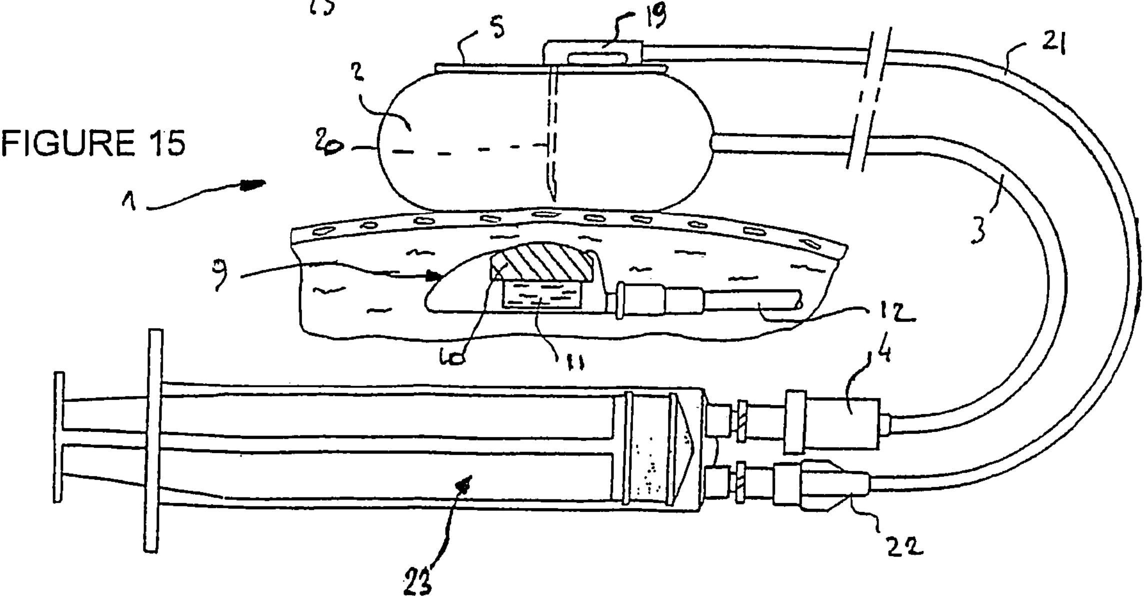

FIGS. 13 through 15 show the different stages in the use of the medical device 1 according to the present invention for implanting and removing the tapered cannula 20 from an implantable chamber 9, for example.

The chamber 9 is implanted under a patient's skin P for treatment by chemotherapy, for example.

The chamber 9 is connected to the outside by way of the cannula 20 which traverses a membrane 10 and opens out inside a recess 11.

The latter is connected by way of a catheter 12 to one of the patient's vessels in order to permit injection of treatment products.

The medical device 1 is placed in such a way that its cannula 20 opens out inside the recess 11 of the implantable chamber 9 located under the skin P.

When the medical device 1 is in the deflated position, the sheath 2 comes to bear against the outer face of the patient's skin P.

Thus, the medical personnel can introduce a treatment product into the inside of the recess 11 of the chamber 9 via the tubing 21 of the cannula 20, so that this product can spread through the patient's blood by way of the catheter 12 connected to an artery.

After introducing the treatment product, the medical personnel can proceed to clean the recess 11 of the implantable chamber 9 by injecting physiological saline, for example, through a syringe 23 connected to the connection system 22.

Simultaneously, with the aid of the same syringe 23 or with the aid of another syringe or a syringe with a Y-shaped connection piece joined to the non-return valve 4, the medical personnel can inject the same liquid into the sheath 2 in order to begin inflating the latter.

The simultaneous injection of physiological saline into the inside of the recess 11 and of the sheath 2 permits rinsing and positive locking of the implantable chamber 9 and of its catheter 12, and also inflation of the sheath 2.

With the chamber 9 positively locked, the volume of the sheath 2 is inflated gradually in order to remove the cannula 20 from the membrane 10 of the implantable chamber 9 and, if appropriate, from the patient's skin P.

Thus, by virtue of the vertical displacement of the disk 5 during the increase in the volume of the sheath 2, the medical device 1 permits introduction of treatment product and gradual removal without risk of a rebound phenomenon and, consequently, without risk of the medical personnel being pricked or injured.

It will also be noted that the sheath 2 of the medical device 1 forms a protective element around the cannula 20 and limits any risk of the medical personnel suffering needlestick injuries.

It will be observed that the medical device 1 according to the present invention makes it possible, by virtue of its inflatable sheath 2, to detach and remove the cannula 13, 20 from the skin.

It must also be understood that the above description has been given only by way of example and does not in any way limit the scope of the invention, and that replacing the embodiment details with any other equivalents would not constitute a departure from the invention.

The invention claimed is:

1. A medical device for removing a tapered cannula (13, 20) forming a needle, the medical device comprising an inflatable sheath (2) connected to a tubing (3), said sheath (2) comprising at least one receiving space (6, 18) for the passage of the cannula (13, 20) in a direction transverse to the lengthwise extent of the needle, wherein when the needle is embedded in a patient, the uninflated sheath can be moved in said direction with the needle moving through said receiving space until the sheath surrounds the needle, after which inflation of the sheath removes the needle from the patient.

2. The medical device as claimed in claim 1, comprising an inflatable sheath (2) connected to a tubing (3), and of a rigid disk (5) forming a horizontal platform arranged and fixed above the sheath (2).

3. The medical device as claimed in claim 2, wherein the inflatable sheath (2) and the rigid disk (5) comprise, respectively, receiving spaces (6, 7, 18) for the passage of the cannula (13, 20).

4. The medical device as claimed in claim 1, wherein the sheath (2) comprises, starting from its center and extending toward the outside, a receiving space formed by a slit (6) creating two separate and leaktight ends, so that said sheath has a C-shaped profile.

5. The medical device as claimed in claim 1, wherein the sheath (2) has a receiving space of annular shape (18).

6. The medical device as claimed in claim 3, wherein the rigid disk (5) comprises, starting from its center, a receiving space formed by a slit (7) having a V-shaped profile whose most open base is arranged toward the periphery of said disk.

7. The medical device as claimed in claim 2, wherein the rigid disk (5) is fixed in the upper part of the sheath (2) in such a way that its center coincides with that of said sheath (2).

8. The medical device as claimed in claim 3, wherein the disk (5) is integral with a body (19) connected to a tapered cannula (20) which traverses said disk so as to cooperate inside the receiving space (18) formed in the sheath (2).

9. The medical device as claimed in claim 8, wherein the body (19) comprises, perpendicular to the cannula (20), a tubing (21) whose free end is integral with a connection system (22).

10. The medical device as claimed in claim 2, wherein the sheath (2) comprises, starting from its center and extending toward the outside, a receiving space formed by a slit (6) creating two separate and leaktight ends, so that said sheath has a C-shaped profile.

11. The medical device as claimed, in claim 3, wherein the sheath (2) comprises, starting from its center and extending toward the outside, a receiving space formed by a slit (6) creating two separate and leaktight ends, so that said sheath has a C-shaped profile.

12. The medical device as claimed in claim 2, wherein the sheath (2) has a receiving space of annular shape (18).

13. The medical device as claimed in claim 3, wherein the sheath (2) has a receiving space of annular shape (18).

* * * * *